United States Patent
Simon

(10) Patent No.: US 11,666,363 B2
(45) Date of Patent: *Jun. 6, 2023

(54) METHOD AND APPARATUS FOR REPAIRING THE MID-FOOT REGION VIA AN INTRAMEDULLARY NAIL

(71) Applicant: Howmedica Osteonics Corp., Mahwah, NJ (US)

(72) Inventor: William H. Simon, Virginia Beach, VA (US)

(73) Assignee: Howmedica Osteonics Corp., Mahwah, NJ (US)

( * ) Notice: Subject to any disclaimer, the term of this patent is extended or adjusted under 35 U.S.C. 154(b) by 198 days.

This patent is subject to a terminal disclaimer.

(21) Appl. No.: 17/143,616

(22) Filed: Jan. 7, 2021

(65) Prior Publication Data

US 2021/0128206 A1    May 6, 2021

Related U.S. Application Data

(63) Continuation of application No. 16/270,800, filed on Feb. 8, 2019, now Pat. No. 10,925,650, which is a
(Continued)

(51) Int. Cl.
*A61B 17/72* (2006.01)
*A61B 17/84* (2006.01)
(Continued)

(52) U.S. Cl.
CPC .......... *A61B 17/7291* (2013.01); *A61B 17/72* (2013.01); *A61B 17/7216* (2013.01);
(Continued)

(58) Field of Classification Search
CPC ... A61B 17/72; A61B 17/725; A61B 17/7225; A61B 17/7233; A61B 17/7291;
(Continued)

(56) References Cited

U.S. PATENT DOCUMENTS 2,614,559 A    10/1952 Livingston
3,709,218 A    1/1973 Halloran
(Continued)

FOREIGN PATENT DOCUMENTS

EP    1095626 A1    5/2001
GB    2308068 A    6/1997
(Continued)

OTHER PUBLICATIONS

John Early, M.D. and Sigvard T. Hansen, M.D., 1996, "Surgical Reconstruction of the Diabetic Foot: A Salvage Approach for Midfoot Collapse", Foot & Ankle International, vol. 17, pp. 325-330 (Year: 1996).*
(Continued)

*Primary Examiner* — Si Ming Ku
(74) *Attorney, Agent, or Firm* — Lerner David LLP

(57) ABSTRACT

A device, method, and system for treatment or fixation of a fractured, damaged, or deteriorating bone or bones in a mid-foot region. The device comprising an implant with both proximal and distal fastener holes, along with fastener slots in a central elongated body, for securing the implant to the appropriate osseous cortical structures of the foot. The method for treatment or fixation of fractured, damaged, or deteriorating bones in the medial column of the foot with use of a device such as an intramedullary nail that attaches to either the talus or first metatarsal bones to secure the medial cuneiform and navicular bones in place.

20 Claims, 3 Drawing Sheets

Related U.S. Application Data continuation of application No. 15/833,118, filed on Dec. 6, 2017, now Pat. No. 10,238,437, which is a continuation of application No. 13/593,987, filed on Aug. 24, 2012, now Pat. No. 9,867,642, which is a continuation of application No. 10/525,544, filed as application No. PCT/US03/24185 on Aug. 1, 2003, now abandoned.

(60) Provisional application No. 60/402,380, filed on Aug. 10, 2002.

(51) Int. Cl.
*A61B 17/88* (2006.01)
*A61B 17/68* (2006.01)

(52) U.S. Cl.
CPC ...... *A61B 17/7225* (2013.01); *A61B 17/7233* (2013.01); *A61B 17/7241* (2013.01); *A61B 17/846* (2013.01); *A61B 17/8897* (2013.01); *A61B 2017/681* (2013.01)

(58) Field of Classification Search
CPC .... A61B 17/846; A61F 2/4202; A61F 2/4225; A61F 2/4241
See application file for complete search history.

(56) References Cited

U.S. PATENT DOCUMENTS

| | | |
|---|---|---|
| 4,409,974 A | 10/1983 | Freedland |
| 4,522,200 A | 6/1985 | Stednitz |
| 4,688,561 A | 8/1987 | Reese |
| 4,705,027 A | 11/1987 | Klaue |
| 4,976,712 A | 12/1990 | VanderSlik |
| 5,034,013 A | 7/1991 | Kyle et al. |
| 5,041,114 A | 8/1991 | Chapman et al. |
| 5,201,735 A | 4/1993 | Chapman et al. |
| 5,336,225 A | 8/1994 | Zang |
| 5,356,410 A | 10/1994 | Pennig |
| 5,505,734 A | 4/1996 | Caniggia et al. |
| 5,549,610 A | 8/1996 | Russell et al. |
| 5,620,445 A | 4/1997 | Brosnahan et al. |
| 5,658,287 A | 8/1997 | Hofmann et al. |
| 5,658,288 A | 8/1997 | Kim |
| 5,683,466 A | 11/1997 | Vitale |
| 5,766,174 A | 6/1998 | Perry |
| 5,814,047 A | 9/1998 | Emilio et al. |
| 5,855,579 A | 1/1999 | James et al. |
| 5,919,193 A | 7/1999 | Slavitt |
| 5,935,127 A | 8/1999 | Border |
| 5,984,681 A | 11/1999 | Huang |
| 5,984,970 A | 11/1999 | Bramlet |
| 6,019,761 A | 2/2000 | Gustilo |
| 6,120,504 A | 9/2000 | Brumback et al. |
| 6,123,708 A | 9/2000 | Kilpela et al. |
| 6,132,362 A | 10/2000 | Tepper et al. |
| 6,193,758 B1 | 2/2001 | Huebner |
| 6,200,321 B1 | 3/2001 | Orbay et al. |
| 6,261,221 B1 | 7/2001 | Tepper et al. |
| 6,261,289 B1 | 7/2001 | Levy |
| 6,270,499 B1 | 8/2001 | Leu et al. |
| 6,406,477 B1 | 6/2002 | Fujiwara |
| 6,406,498 B1 | 6/2002 | Tormala et al. |
| 6,533,788 B1 | 3/2003 | Orbay |
| 6,569,165 B2 | 5/2003 | Wahl et al. |
| 6,572,620 B1 | 6/2003 | Schon et al. |
| 6,576,018 B1 * | 6/2003 | Holt ...................... A61B 17/68 606/328 |
| 6,579,293 B1 | 6/2003 | Chandran |
| 6,629,976 B1 | 10/2003 | Gnos et al. |
| 6,719,801 B1 | 4/2004 | Holt |
| 7,001,388 B2 | 2/2006 | Orbay et al. |
| 7,247,156 B2 | 7/2007 | Ekholm et al. |
| 7,314,488 B2 | 1/2008 | Reiley |
| 7,410,488 B2 | 8/2008 | Janna et al. |
| 7,425,213 B2 | 9/2008 | Orbay |
| 7,717,947 B1 | 5/2010 | Wilberg et al. |
| 7,722,611 B2 | 5/2010 | Cavallazzi et al. |
| 7,780,664 B2 | 8/2010 | Orbay |
| 7,867,231 B2 | 1/2011 | Cole |
| 7,892,234 B2 | 2/2011 | Schlienger et al. |
| 7,951,176 B2 | 5/2011 | Grady, Jr. et al. |
| 3,048,164 A1 | 11/2011 | Reiley |
| 8,083,742 B2 | 12/2011 | Martin |
| 8,182,485 B1 | 5/2012 | Gonzalez-Hernandez |
| 8,216,239 B2 | 7/2012 | Munro et al. |
| 8,262,658 B2 | 9/2012 | Schlienger et al. |
| 8,313,488 B2 | 11/2012 | Schlienger et al. |
| 8,343,199 B2 | 1/2013 | Tyber et al. |
| 8,361,075 B2 | 1/2013 | Gonzalez-Hernandez |
| 8,496,712 B2 | 7/2013 | Reiley |
| 8,518,040 B2 | 8/2013 | Schlienger et al. |
| 8,540,715 B2 | 9/2013 | Piraino |
| 8,679,119 B2 | 3/2014 | Lopez-Oliva Munoz |
| 8,734,448 B2 | 5/2014 | Thakkar |
| 8,747,480 B2 | 6/2014 | Cachia |
| 8,906,024 B2 | 12/2014 | Schlienger et al. |
| 8,971,984 B2 | 3/2015 | Freeman et al. |
| 9,066,764 B2 | 6/2015 | Perez |
| 2001/0049530 A1 | 12/2001 | Culbert et al. |
| 2002/0029041 A1 | 3/2002 | Hover et al. |
| 2002/0068939 A1 | 6/2002 | Levy et al. |
| 2003/0097131 A1 | 5/2003 | Schon et al. |
| 2003/0130660 A1 | 7/2003 | Levy et al. |
| 2003/0135212 A1 | 7/2003 | Chow |
| 2004/0039394 A1 | 2/2004 | Conti et al. |
| 2004/0220570 A1 | 11/2004 | Frigg |
| 2004/0260297 A1 | 12/2004 | Padget et al. |
| 2005/0069397 A1 | 3/2005 | Shavit et al. |
| 2005/0107791 A1 | 5/2005 | Manderson |
| 2006/0041262 A1 | 2/2006 | Calvert et al. |
| 2006/0100623 A1 | 5/2006 | Pennig |
| 2006/0111716 A1 | 5/2006 | Schlienger et al. |
| 2006/0206044 A1 | 9/2006 | Simon |
| 2009/0306666 A1 | 12/2009 | Czartoski et al. |
| 2010/0057133 A1 | 3/2010 | Simon |
| 2010/0256638 A1 | 10/2010 | Fyber et al. |
| 2010/0256685 A1 | 10/2010 | Plecko et al. |
| 2011/0118739 A1 | 5/2011 | Fyber et al. |
| 2011/0118792 A1 | 5/2011 | Orsak |
| 2011/0118796 A1 | 5/2011 | Reiley et al. |
| 2011/0125153 A1 | 5/2011 | Tyber et al. |
| 2011/0230884 A1 | 9/2011 | Mantzaris et al. |
| 2012/0330313 A1 | 12/2012 | Grady et al. |
| 2013/0030434 A1 | 1/2013 | Tyber et al. |
| 2013/0053848 A1 | 2/2013 | Tyber et al. |
| 2013/0150903 A1 | 6/2013 | Vincent |
| 2013/0172889 A1 | 7/2013 | Tyber et al. |

FOREIGN PATENT DOCUMENTS

| | | |
|---|---|---|
| JP | H07-213535 A | 8/1995 |
| WO | 199944685 A1 | 9/1999 |
| WO | 0038586 A1 | 7/2000 |
| WO | 0072767 A1 | 12/2000 |
| WO | 0234107 A2 | 5/2002 |

OTHER PUBLICATIONS

International Search Report for PCT/US03/24185 dated Jan. 15, 2004.

Frykberg, R.; "The High Risk Foot in Diabetes Mellitus"; 1991; CH. 16, p. 297, Churchill Livingstone Inc., New York, NY.

John Early, M.D. and Sigvard T Hansen, M.D., 1996, "Surgical Reconstruction of the Diabetic Foot: A Salvage Approach for Midfoot Collapse", Foot & Ankle International, vol. 17, pp. 325-330.

Lewis et al., "Geometrical Properties and Torsional Fatigue Life of a Tibial Interlocking Intramedullary Nail Segment" Journal of Orthopedic Trauma, vol. 12, No. 1, Jan. 1998, pp. 8-15.

(56) References Cited

OTHER PUBLICATIONS

Schandelmaier et al., "Biomechanical Study of Nine Different Tibia Locking Nails" Journal ofOrthapedic Trauma, vol. 10, No. I, Jan. 1996, pp. 37-44.
Pinzur et al., "Charcot Ankle Fusion with a Retrograde Locked Intramedullary Nail", Foot & Ankle International, vol. 18, No. 11, Nov. 1997, 6 pages.
Simon et al., "Arthrodesis as an Early Alternative to Nonoperative Management of Charcot Arthopathy of the Diabetic Foot", The Journal of Bone and Joint Surgery, Inc., S.R. SimonEt Al., vol. 82-A, No. 7, Jul. 2000, pp. 939-950.
Chi et al., "The Lateral Column Lengthening and Medial Column Stabilization Procedures" Clinical Orthopedics and Related Research, T. D. Chi Et al., No. 303, Aug. 1999, pp. 81-90.
"The Titanium Cannulated Hindfoot Arthrodesis Nail, Expert Nailing System, Technique Guide," Synthes, 2007, 47 pages.
"6.5 mm Midfoot Fusion Bolt. For intramedullary fixation of the medial column of the foot.," Technique Guide, Synthes, Inc., 2009, 30 pages.
Early, J. et.al., "Surgical Reconstruction of the Diabetic Foot: A Salvage Approach for Midfoot Collapse", Foot & Ankle International, vol. 17, No. 6, Jun. 1996, pp. 325-330.

\* cited by examiner

METHOD AND APPARATUS FOR REPAIRING THE MID-FOOT REGION VIA AN INTRAMEDULLARY NAIL

CROSS-REFERENCE OF RELATED APPLICATIONS

The present application is a continuation of U.S. patent application Ser. No. 16/270,800 filed Feb. 8, 2019, which is a continuation of U.S. patent application Ser. No. 15/833,118 filed Dec. 6, 2017, now U.S. Pat. No. 10,238,437, which is a continuation of U.S. patent application Ser. No. 13/593,987 filed Aug. 24, 2012, now U.S. Pat. No. 9,867,642, which is a continuation of U.S. patent application Ser. No. 10/525,544 filed Jan. 28, 2005, published as U.S. Patent Application Publication No. 2006/0206044 A1 and now abandoned, which is a national phase entry under 35 U.S.C. § 371 of International Application No. PCT/US2003/024185 filed Aug. 1, 2003, published as International Publication No. WO 2004/014243 A1, which claims priority from U.S. Provisional Patent Application No. 60/402,380 filed Aug. 10, 2002, all of which are incorporated herein by reference.

BACKGROUND OF THE INVENTION

Field of the Invention

The field of the present invention relates to a method and apparatus for repairing damaged, deteriorating, or fractured bones in the mid-foot region. More particularly, the present invention relates to both a method and device for treating the bones in the medial column of a human foot that are effected by Diabetic Charcot mid-foot collapse, LisFranc injuries, and the like.

Description of Related Art

The utilization of implants, such as intramedullary nails, rods, and screws is well known in the art, specifically in the treatment of long or large bone fractures. Implants are those devices which may be inserted into any foreign body, with intramedullary nails being the most common type of implant. Intramedullary nails have been limited in their application to long or large bones and such use has been widely known for long or large bones of the upper extremities (humerus, radius, ulna) and lower extremities (femur, tibia, fibula). Use of intramedullary nails allows physicians to secure fractured bones, maintain a desired length, and prohibit rotary motion while the bone heals and has time to rehabilitate. Intramedullary nails are also used for the fusion of bones.

Intramedullary nails are adapted for insertion into the medullary canal of a bone or bones, which may be reamed or left unreamed. Reaming is achieved by drilling out the medullary canal of the fractured or deteriorating bone, where the nail is inserted to stabilize and position the bone for healing. A cannulated reamer diameter generally runs in size from 7 mm and 18 mm, at increments of 0.5 mm A medullary canal is generally reamed at 0.5 mm larger than the diameter of the nail to be inserted, so the bone is not damaged when the nail is inserted. Such reamers are well known by those with skill in the art.

Much of the prior art implant and intramedullary nail systems comprise intramedullary nails having fastener holes at both the proximal and distal ends for the insertion of fasteners, or locking screws. Fasteners include all attaching means by which an implant may be attached to bone. Such fasteners are inserted through a fastener hole or slot, also described as transfixation holes and screw holes. The use of locking screws is optional depending upon the severity of the bone damage. An intramedullary nail implanted with at least one fastener or locking screw both proximally and distally completely locks the nail in place (also known as static locking). Static locking neutralizes rotational stresses while preventing shortening of the limb. An intramedullary nail implanted with only one locking screw either proximally and distally, partially locks the nail (also known as dynamic locking). Dynamic locking neutralizes rotational stresses on one side of the fracture site while permitting axial loading. To surgically promote fusion of bone segments together, some means of static locking is required. Such holes and screws may also be adapted for the central portion of the nail or implant.

Several nails exist with fasteners or locking screws that are much longer in shape, described as lag screws, jigs, or nail heads, which further prevent the rotation of separated bones. Other nails have spacers to absorb stress associated with repetitive, natural impact. All such devices are focused on securing bone fragments during the process of fracture healing. Other methods for attaching the nail to the bone including the use of longitudinal pins, or the use of cement injected through a cannula in a nail to secure one end to the nail.

Various types of implants and intramedullary nails exist in the prior art, each composed of different materials and having different shapes with various degrees of functionality. Many nails are formed from either a slid rod metal or a more flexible sheet metal. Several nails have been proposed which form a rod material containing a central longitudinal bore disposed throughout (cannulated). Many nails have a number of longitudinal grooves cut along the rod (known as fluting), which allow for more rapid revascularization within the bone. Accordingly, nails made of various material and those having a differing array of shapes already exist and may be easily manufactured. A study of the geometrical properties of different nails is discussed in the article "*Geometrical Properties and Torsional Fatigue Life of a Tibial Interlocking Intramedullary Nail Segment*" Journal of Orthapedic Trauma, Vol. 12, No. 1, pp 8-15, and is incorporated herein. Also, different tibial nails were compared in the article "*Biomechanical Study of Nine Different Tibia Locking Nails*" Journal of Orthapedic Trauma, Vol. 10, No. 1, pp 37-44, which is also incorporated herein.

Recently, implants and intramedullary nails are being fabricated using bioactive, biocompatible, and bioabsorbable material. Such nails are made from bioabsorbable polymers, copolymers, or polymer alloys that are self-reinforced containing ceramic particles or some type of reinforcement fibers. These implants and nails, as well as others, can also be made to be porous. The knowledge exists today to create human replica bones, grown in animals utilizing human gene technology, for ultimate use in humans, and such material may be a viable supplement for standard intramedullary nails of today. Such techniques should also be considered as an appropriate part of the present invention.

While there is much in the art regarding implants and intramedullary nails, there was no prior art found dealing directly with implants or intramedullary nails for the mid-foot region, or medial column of a human foot. Such a nail may likely have any or all of the similar properties, features, and characteristics of the above mentioned nails, but would have to be much smaller in length and thickness (for axial support) to accommodate the smaller bones of the mid-foot region. The prior art referring to intramedullary nails, for the most part, refers to nails which are used in much larger bones. Such art includes:

WO 00/72767 A1. The application describes an intramedullary nail for insertion within an intramedullary canal of a long bone and fixing a fracture in the long bone. The nail comprises an elongate member with longitudinal axis, proximal and distal end, both of which have fastener receiving areas of at least one hole.

U.S. Pat. No. 6,406,477. The patent describes an intramedullary nail with a lag screw for connecting a bone portion separated from the femur, by fracture, to the main portion of the bone where such nail is capable of extending through both portions where a lag screw secures the nail.

WO 02/34107 A2. The Application describes an internal fixation device which utilizes a shaft within a sleeve wherein the shaft is movable within the sleeve along aligned slots.

U.S. Pat. No. 6,270,499 B1. The patent describes an intramedullary nail where the proximal end has at least one bore which extends transversely to the central axis of the nail for receiving at a stable angle a bone fastener.

U.S. Pat. No. 6,406,498 B1. The patent describes a device, such as an intramedullary nail or the like, which is fabricated using bioactive, biocompatible, and/or bioabsorbable material.

U.S. Patent Application No. US 2002/0029041 A1. The application describing an intramedullary nail formed with opposing dynamization windows and spacers of nonmetal material positioned within the windows to absorb stress transmitted through a fracture site.

U.S. Pat. No. 6,120,504. The patent describes an intramedullary nail with a longitudinal centerline extending between a proximal and distal end. The invention is directed to be interchangeably used in either a right or left limb, and to thus reduce the number of nail that must be inventoried at hospitals and other places utilizing intramedullary nails.

U.S. Pat. No. 4,705,027. The patent describes an intramedullary nail having a slot at the tip of the nail for engaging within the slot, a bolt previously inserted into the bone.

U.S. Pat. No. 5,658,287. The patent describes a locked intramedullary nail suitable for treating fractures of the femur.

U.S. Pat. No. 5,034,013. The patent describes an intramedullary nail having a tubular elongated body with grooves along the elongated body to allow for improved revascularization about the nail.

U.S. Pat. No. 5,766,174. The patent describes an intramedullary nail with an arcuate terminus tip, transverse holes for receiving fixation screws, and suture holes for the attachment of tissue.

U.S. Pat. No. 5,336,225. The patent describes device for reducing fractures, comprising a threaded screw.

U.S. Pat. No. 6,123,708. The patent describes a nail for axial insertion into a bone for support comprising a central bore through the nail body and a plurality of transverse holes throughout.

U.S. Pat. No. 5,814,047. The patent describes an intramedullary nail fixation apparatus having a plurality of equiangularly spaced piercing points.

U.S. Pat. No. 5,855,579. The patent describes a modular intramedullary nail having an open ended longitudinal bore, with connectable ends for elongating the nail.

EP 1095626 A1. The patent describes a radial intramedullary nail.

U.S. Pat. No. 5,620,445. The patent describes a modular intramedullary nail with proximate, distal, and central components.

There is no known prior art relative to the use of intramedullary nails in the treatment of mid-foot bones or more specifically, treating the bones of the medial column. Most of the prior art describing the use of intramedullary nails is limited to methods for repairing large bones including, but not limited to the humerus, radius, ulna, femur, tibia, and fibula. Such art includes:

U.S. Pat. No. 6,019,761. The patent describes an intramedullary nail for implanting within a patient's long bone, and a method of use.

U.S. Pat. No. 5,201,735. The patent describes an apparatus such as a bone implant and method for implanting a bone implant or intramedullary rod for fixing a fracture of a bone.

U.S. Pat. No. 5,935,127. The patent describes a method for treating a fracture in a long bone by utilizing either a plate or intramedullary nail that spans the length of the bone.

U.S. Pat. No. 5,919,193. The patent describes a method for surgically correcting malformations in digits of a finger or toe by way of a one piece bone screw.

U.S. Pat. No. 4,976,712. The patent describes a method and apparatus for treating fractured bones by way of a bone screw.

The prior art relative to current treatments of mid-foot deformities, particularly those analogous to this type of treatment, are limited to:

"Charcot Ankle Fusion with a Retrograde Locked Intramedullary Nail" Foot & Ankle International, Vol. 18, No. 11, November 1997. This article focuses primarily on ankle fusion with a locked intramedullary nail, but specifies mid-foot deformity treatment to be limited to patient education, local foot-care, accommodative shoe gear, custom foot orthoses, and surgical correction.

Additional articles of significance include; "Surgical Reconstruction of the Diabetic Foot: A salvage approach for mid-foot collapse" Foot Ankle Int., Early, J. S. and Hansen, S. T., 17:325-330, 1996 and "Arthrodesis as an Early Alternative to Nonoperative Management of Charcot Arthopathy of the Diabetic Foot", The Journal of Bone and Joint Surgery, Inc., S. R. Simon Et Al., Vol. 82-A, No. 7, July 2000.

"The Lateral Column Lengthening and Medial Column Stabilization Procedures" Clinical Orthopedics and Related Research, T. D. Chi Et al., No. 303, August 1999. Is an article that is the closest related study of surgical repair procedures to the present invention; however, it describes the use of multiple screws to secure the bones within the mid-foot which produced severely limited results.

BRIEF SUMMARY OF THE INVENTION

The present invention is directed to a device and method for treating and fixation of deteriorating, damaged, or fractured bones in the mid-foot region (navicular, medial cuneiform, intermediate cuneiform, lateral cuneiform and cuboid bones). More specifically, the present invention relates to the treatment and fixation of certain bones in the medial column (specifically, the medial cuneiform and navicular bones) of a human foot. Such bones are not considered long or large in the traditional sense as are those specified above. An apparatus, such as an implant, or more specifically an intramedullary nail, is inserted through and attached to both the first metatarsal and talus bones to secure the medial cuneiform and navicular bones in place. This procedure also is expected stabilize all the bones in the mid-foot region.

After appropriate reduction and compression, such a method and device would ultimately allow for fusion of the bones. In accordance with the present invention, one device used to achieve the above described method is a cannulated intramedullary nail that is round in cross-section, having an elongated body with a proximal head portion, intermediate portion, and distal tapered end portion. The proximal head portion has one or more transverse holes, ideally three, with an intermediate portion having one or more transverse slots, ideally two, and a distal portion having one of more transverse holes, ideally two. Such transverse fastener holes or slots are used for insertion of fasteners (including interlocking cortical screws or transfixation screws), which ideally may be attached to the first metatarsal and talus bones to secure the nail in place. Slots are adapted for the central portion of the nail for the insertion of fasteners into either the navicular or medial cuneiform, depending upon the condition of either of the two bones.

One object of the present invention is to provide an implant or intramedullary nail for the treatment and fixation of those bones within the mid-foot that are subject to damage, deterioration, or fracture that may result from diabetes related diseases, including but not limited to, Charcot foot. More than 16 million Americans have diabetes, of which approximately 54,000 patients underwent lower extremity amputations in 1990. The five-year mortality rate for diabetics has been reported as high as 70%. Approximately 800,000 Americans develop diabetes annually. The cost of caring for diabetes now exceeds $137 billion per year, or approximately 30% of the annual Medicare budget. Diabetic neuropathy ultimately results in deterioration of the bones in the foot. Such deterioration of those bones in the mid-foot region leads to the collapse of the foot, fracture of those bones, or both. The prevalence of Diabetic Charcot joints has been reported to be from 0.08% to 7.5%. The average age of onset is approximately 57 years with the majority of patients in their sixth and seventh decades. The average duration of diabetes with a diagnosis of Charcot arthropathy is 15 years, with 80% of the patents being diabetic for more than 10 years. Bilateral Charcot arthropathy has been reported between 5.9% to 39.9%. Incidence of Diabetic Charcot arthropathy appears equally among men and women.

Diabetic foot treatment to date has been limited to amputation, special casts or shoes which alleviate the deformity, and surgical intervention to strengthen the foot. An article describing an overview of diabetic foot problems is "*Diabetic Neuropathic Osteoarthropathy: The Charcot Foot*" Chapter 16 of *The High Risk Foot in Diabetes Mellitus*, edited by R. G. Frykberg,© Churchhill Livingstone Inc., 1991, and is incorporated herein Amputation of the opposite extremity is frequently indicated within one to five years of the primary amputation. Surgical intervention has been restricted to the use of screws and plates since most bones in the foot are quite small. Methods used to repair larger bones with devices such as intramedullary nails have not been utilized in this area until now.

The medial column of the foot is comprised of six osseous components (distal phalanx, proximal phalanx, first metatarsal, medial cuneiform, navicular, and talus). The longitudinal arch of the foot is maintained by these bone segments and their supporting ligaments, tendons, and surrounding musculature. Additional support comes from the transverse arch and the interlocking of the osseous components. The medial column of the foot is the most commonly affected in the diabetic by sympathectomy-induced hyperemia associated with repetitive minor trauma resulting in mid-foot dislocations and/or fractures known as Diabetic Charcot deformities.

Treatment of foot and ankle Charcot deformities currently consists of nonsurgical (non-contact casting, orthotic bracing, and shoe gear) and surgical stabilization (k-wires, screw/plate fixation, and external fixators). Recently, implant and intramedullary nail fixation has been utilized to stabilize the ankle/subtalar joint complex. Present treatment for medical column/mid-foot deformities requires extensive surgical exposure with appropriate internal screw/plate fixation devices. One advantage of using an implant or intramedullary nail for treatment and fixation of these bones, is the limited surgical exposure that is required with only several small incisions, as opposed to the more invasive exposure resulting from opening the entire foot for insertion of several internal screws and plate devices. Also, the successes of screw and plate fixation is minimal at best.

Although prior art nails have found varying degrees of success in the treatment of long bone fractures and hind-foot arthrodesis, there remains a need in the field for an intramedullary nail specific for fixation of the medial column of the foot. This device will substantially reduce, if not eliminate many of the present complications encountered with Diabetic Charcot foot reconstruction. Such a device would provide fixation and stabilization of the Diabetic Charcot foot preventing future mid-foot collapse and ultimate limb loss. An intramedullary medial column nail and method of utilization would provide stabilization to the medial column of the foot, eliminating excessive operating time, anesthesia exposure, implant failure, long hospital stays, and reduce overall medical cost leading to early rehabilitation and ultimately limb salvage.

The present invention specifically relates to the fusion, and eventual rejuvenation of the bones in the mid-foot region which deteriorate because of diabetic neuropathy. The method comprises insertion of an implant or intramedullary nail through the medial cuneiform and navicular bones, which are most susceptible to deterioration, and securing the nail with locking screws to the stable first metatarsal and talus bones. This is one method for securing, fusing, and repairing the medial cuneiform and navicular bones and represents one embodiment of the present invention.

The present invention utilizes an intramedullary medial column nail fixation apparatus ideally being cylindrical and cannulated, and made from either titanium, a bioabsorbable material, human or animal bone, or equivalent. The nail ideally would have a number of proximal and distal fastener holes (transfixation or interlocking holes) for securing the IM medial column nail to the appropriate osseous cortical structures of the foot. An important feature of the present invention of the IM nail is its ability to function as an internal load-sharing device along the medial column of the foot. The nail acts as an internal splintage while the bones are mending, and is used to bring into alignment microfractures that may exist. The proximal portion of the nail may have a tapered tip to aid in insertion, and at least one fastener hole (ideally two) for the insertion of fasteners to fixate the neck of the talus to the implant or nail. The intermediate portion ideally has two slots to accommodate for any bone loss of the navicular and medial cuneiform, and to allow for the possible insertion of a fastener if the bones are healthy enough. The distal portion has at least one fastener hole (ideally three) for the insertion of fasteners to fixate the nail to the first metatarsal.

The present invention may also make use of a specialized thin walled tubular chisel system for removal of first metatarsal head articular cartilage for nail insertion 30. This maintains the integrity of the first metatarsal head by removing only an appropriate sized plug of bone according to the diameter of nail being used. The plug of articular cartilage and underlying bone can then be replaced and fixated after insertion of the nail. Such a chisel system may be similar to one that has been used in osteochonral autograph transfer.

In addition, another embodiment of the present invention calls for the use of a compression system that incorporates a depth gauge device which may be used to determine the amount of compression achieved. This device would eliminate the need for guessing or "feeling" the correct amount of compression required. A depth gauge would exist either on the implant or jig apparatus with a ruler type measuring means for gauging the amount of travel in the nail back up the intramedullary canal towards the phalanges. Compression could then be determined to a specified length of travel of the nail back up the canal during compression.

DETAILED DESCRIPTION

The following description will explain the embodiments of the invention, beginning with a device used for treating deteriorating or damaged bones in the medial column of a human foot, and concluding with the method for treating deteriorating or damaged bones in the medial column of a human foot. Both the first and second figures are skeletal outlines of a human foot, depicting the device therein and the resulting orientation of the bones by using the method specified below.

Figure 1:
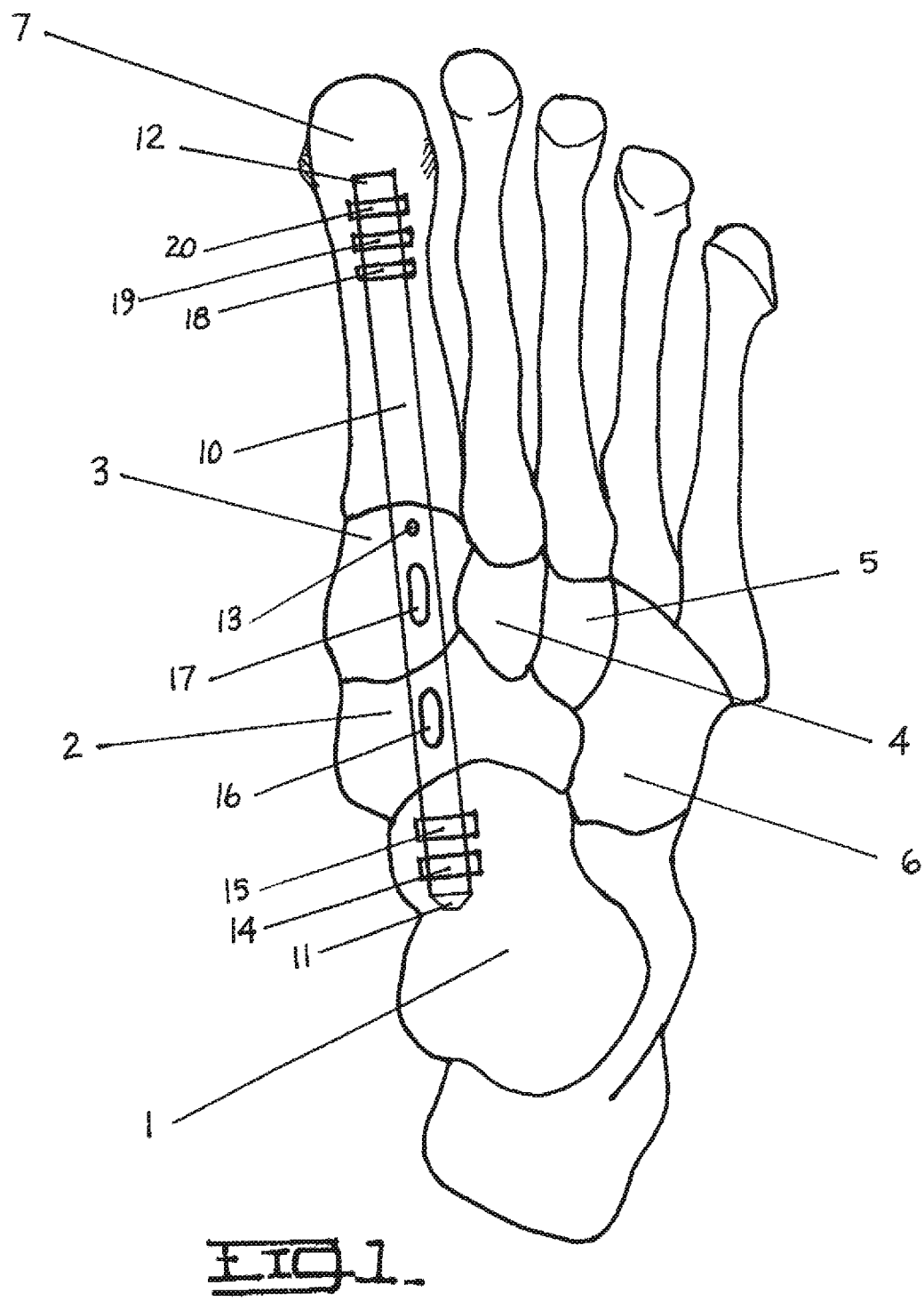
FIG. 1 is a top down skeletal outline of a right human foot with an implant located within.

FIG. 1 is a top down view of a right human foot, depicting the bones therein and an implant or intramedullary nail 10 running through the mid-foot region. The implant or intramedullary nail 10 runs through the medullary canal of first metatarsal 7, medial cuneiform 3, navicular 2, and talus bone 1. The talus bone 1 makes up the lower part 20 of the ankle joint where the proximal end 11 of the implant or intramedullary nail 10 is attached with at least one fastener (or locking screw, with two depicted in FIGS. 1, 14 & 15). Next to the talus bone, opposite the rest of the ankle bones, are the tarsal bones which include the navicular 2, medial cuneiform 3, intermediate cuneiform 4, lateral cuneiform 5, and cuboid bones 6. The medial cuneiform 3 and navicular 2 bones are those most affected by the Diabetic Charcot foot disorder, which causes deterioration and possible collapse as a result of the mechanics behind the foot and the amount of weight they are responsible for. These are the bones that the present invention focuses on fixation and stabilizing for rejuvenation, and insertion of an implant or intramedullary nail 10 through them as an embodiment of the invention. If either of the two bones are stable enough to support a locking screw, the nail is designed to have holes for that purpose, a first fastener hole 16 for the navicular bone 2 and a second fastener hole 17 for the medial cuneiform 3. These two fastener holes transverse the axial central axis (central elongated body) 13 of the nail. Finally, the first metatarsal 7 is the bone that makes up the big toe in the human foot, where the distal end 12 of the intramedullary nail 10 is attached by way of at least one fastener (or locking screw, with three depicted in FIGS. 1, 20, 19, and 18).

Figure 2:
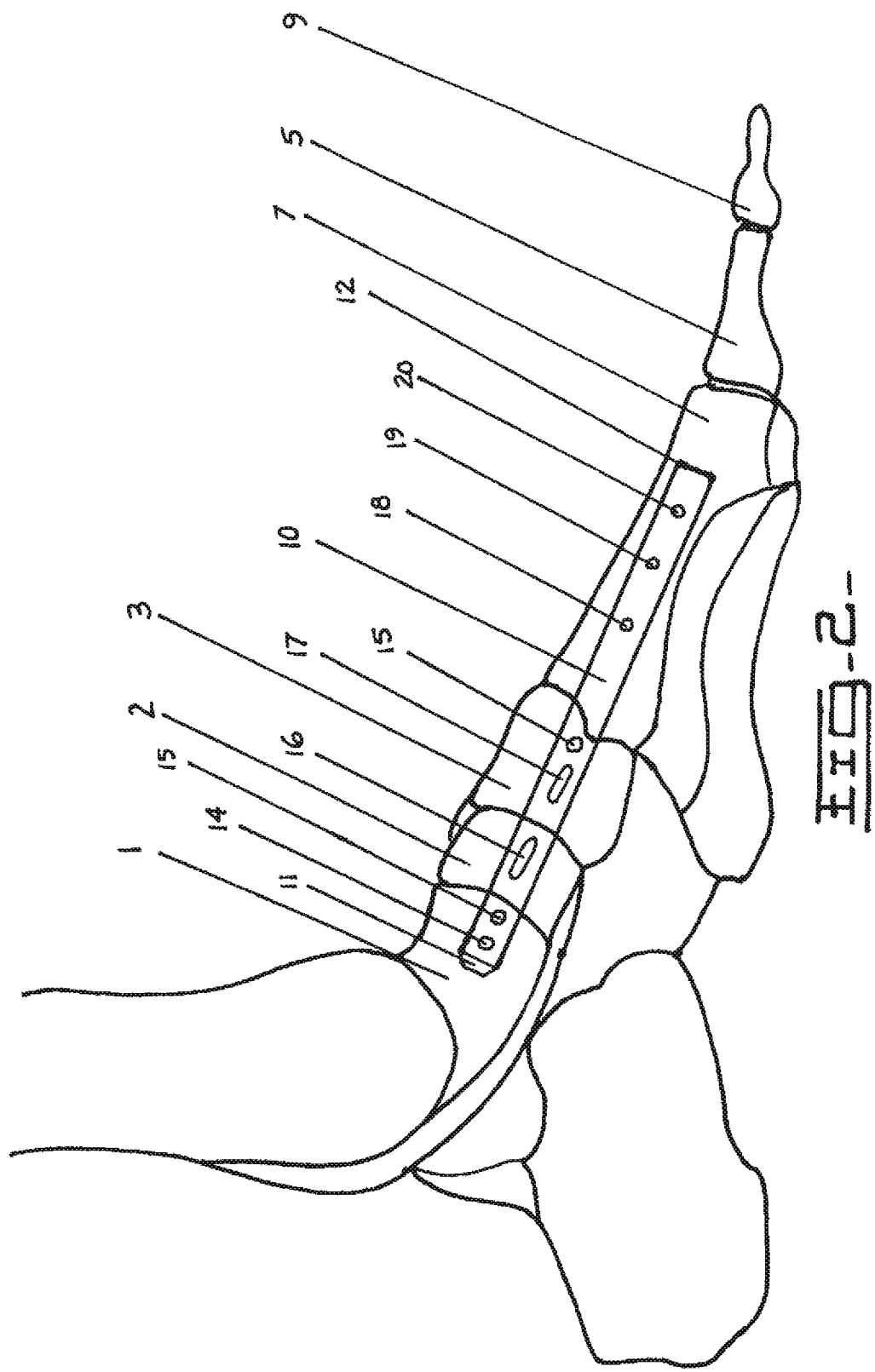
FIG. 2 is a side skeletal outline of a left human foot with an implant located within.

FIG. 2 is a side view of a left human foot, depicting the bones therein and an implant or intramedullary nail 10 running through the mid-foot region. Again, the implant or intramedullary nail 10 runs through the medullary canal of first metatarsal 7, medial cuneiform 3, navicular 2, and talus bone 1. This figure shows the phalanges bones (8 & 9) which are joined to the first metatarsal 7, at which the joint must be dislocated downward (as will be discussed below) prior to insertion of the intramedullary nail 10. Proximal end 11 of nail 10 defines a chamfer such that the implant may be inserted up into the talus bone 1 far enough so that at least one of proximal fastener holes (14 & 15 depicted) are within the bone.

The nail 10, being one embodiment of the present invention, must be sized (length and diameter) so that it extends far enough into the talus bone 1 to clear at least one fastener hole, and include fastener holes for the proper attachment of fasteners (locking screws) in the remaining bones, at least one fastener hole (with three depicted in the FIGS. 20, 19, & 18) for attaching and locking the nail to the first metatarsal 7, and optionally, a first fastener hole 16 for the navicular bone 2 and a second fastener hole 17 for the medial cuneiform 3.

A second embodiment of the present invention is the method by which a device (such as an intramedullary nail as depicted in FIG. 1 & FIG. 2) may be used and inserted into and through the mid-foot region to support damaged or deteriorating bones therein. The first step would consist of the taking of x-ray pictures of the unhealthy foot to determine the extent of the injury, and the size (length and diameter) of the device or implant (herein, intramedullary nail 10, as depicted in FIG. 1 & FIG. 2) needed for insertion. Second, dislocation of the phalanges 8 which are attached to the first metatarsal must be done to expose the head of the first metatarsal. Third, an arthrotomy of the first metatarsal 7 is done. Fourth, as an optional embodiment of the present invention, a tubular chisel system may be used to remove a plug of bone and cartilage from the underlying head of the first metatarsal (which can then be re-plugged after insertion of the nail to more rapidly promote healing and not leave a gap in the head of the bone as one skilled in the art would recognize). Fifth, closed reduction is performed on the bones in the mid-foot region which may be sagging or close to collapse as a result of deterioration or fracture. Sixth, a guide-wire is inserted through the medullary canal of first metatarsal 7, medial cuneiform 3, navicular 2, all the way into the talus 1 with use of fluoroscopy to maintain correct alignment of the foot. The first guide-wire may have a ball tip on the end to make sure the flexible reamer may be easily removed if it breaks. The seventh step consists of reaming over the guide-wire with the ball tip all the way into the talus 1. The reaming is done under fluoroscopy so that the correct depth into the talus 1 may be achieved. Reaming should be done at 0.5 mm diameter larger than the nail to be inserted. The eighth step consists of placing the appropriate sized nail into a jig apparatus with outrigger, and then inserting the nail into the first metatarsal 7, by running over a smooth guide-wire. The nail is centered into the medullary canal beginning with the first metatarsal 7, and then through the medial cuneiform 3, navicular 2, and talus 1 bones respectively. Ninth, at least one fastener (or locking screw, with two depicted in FIGS. 1, 14 & 15) is placed percutaneously into the proximal fastener hole of the nail, and into the talus bone. This procedure only requires a small stab incision, that which one "skilled in the art" would appreciate. The tenth step, is an optional step of compression that may be achieved with a nail of the type having a trocar and sleeve mechanism known in the art, or the like. A further embodiment of the present invention could include a depth gauge device which may be used to determine the amount of compression achieved, that which is determined by the width of the bone. This device would eliminate the need for guessing the correct amount of compression required, since the amount of compression could then be determined to a specific length of travel of the nail back up the canal. An in-line compression sleeve may be one means used to afford compression upon the bones in the mid-foot region. After adequate compression is achieved (that which would be known by those skilled in the art), the eleventh step involves insertion of at least one fastener (or locking screw, with three depicted in FIGS. 1, 20, 19, & 18) into the distal fastener hole(s) and also into the first metatarsal. The same process of percutaneously inserting the fasteners as noted above for the proximal end can be replicated here. Fasteners may be optionally included in slots 16 for the navicular bone 2 and 17 for the medial cuneiform 3, depending upon the condition of either of these two bones. The twelfth step consists of removing the jig and replacing the plug of bone previously removed (if such step was utilized). The joint is then reduced (relocated) and the joint capsule is repaired and the sites are all sutured.

Figure 3:
FIG. 3 is an x-ray picture taken following an experimental procedure to insert an implant into a patient's foot.

FIG. 3 is an x-ray picture taken following an experimental procedure to insert an implant into a patient's foot with two fasteners at both the proximal and distal ends. The procedure, performed in March of 2000, is being followed-up to determine the effectiveness of the newly adapted treatment. This is the only procedure to date ever performed of its kind. Such a procedure is an embodiment of the present invention.

The implant was a small intramedullary (Smith & Nephew) nail intended for insertion in a longer bone. The fasteners were locking screws inserted into the transfixation holes and also into the talus and first metatarsal bones. Such a device is an embodiment of the present invention.

The invention claimed is:

1. A surgical method comprising the steps of:
inserting a one-piece, monolithic first implant into a plurality of bones in a mid-foot region of a foot; and
extending a second implant into the first implant to secure the first implant to the foot with a first threaded connection to a first bone of the foot.

2. The surgical method of claim 1, further comprising a step of securing the second implant to the foot, the first implant being attached to the second implant.

3. The surgical method of claim 1, further comprising a step of securing the first implant to the foot with a second threaded connection to the foot.

4. The surgical method of claim 3, wherein the second threaded connection secures the first implant to a second bone of the foot different from the first bone.

5. The surgical method of claim 3, wherein the first implant is secured to a first metatarsal of the foot.

6. The surgical method of claim 1, wherein the step of extending the second implant into the first implant includes inserting a first fastener into a first hole of the first implant, wherein the first fastener provides the first threaded connection.

7. The surgical method of claim 6, further comprising the steps of:
inserting a second fastener into a second hole of the first implant; and
securing the first implant to the foot with a second threaded connection between the second fastener and a second bone of the foot.

8. A surgical method comprising the steps of:
inserting an intramedullary nail into a plurality of bones in a mid-foot region of a foot; and
securing the intramedullary nail to the foot with a first threaded connection to a first bone of the foot.

9. The surgical method of claim 8, further comprising a step of securing the intramedullary nail to the foot with a second threaded connection to the foot.

10. The surgical method of claim 9, wherein the second threaded connection secures the intramedullary nail to a second bone of the foot different from the first bone.

11. The surgical method of claim 9, wherein the intramedullary nail is secured to a first metatarsal of the foot.

12. A surgical method comprising the steps of:
securing a first implant extending within a mid-foot region of a foot with a first threaded connection to a first bone in the mid-foot region of the foot, the first implant extending within a plurality of bones of the mid-foot region of the foot and through a joint between the plurality of bones; and
securing the first implant with a second threaded connection to a second bone in the foot different from the first bone, wherein the first and the second threaded connections are made by threads separated by an unthreaded portion of the first implant.

13. The surgical method of claim 12, wherein the plurality of the bones of the mid-foot region of the foot includes the first and the second bones of the foot.

14. The surgical method of claim 12, wherein the second bone is a first metatarsal of the foot.

15. The surgical method of claim 12, wherein the second bone is a medial cuneiform of the foot, a navicular bone of the foot, or a talus bone of the foot.

16. The surgical method of claim 12, wherein the first implant is an intramedullary nail.

17. The surgical method of claim 12, further comprising the steps of:
aligning a first hole of the first implant with a first metatarsal of the foot, a medial cuneiform of the foot, a navicular bone of the foot, or a talus bone of the foot; and
aligning a second hole of the first implant with the first metatarsal of the foot, the medial cuneiform of the foot, the navicular bone of the foot, or the talus bone of the foot.

18. The surgical method of claim 17, further comprising the steps of:
inserting a first fastener through the first hole; and
inserting a second fastener through the second hole.

19. The surgical method of claim 12, wherein the first implant is a one-piece, monolithic implant.

20. The surgical method of claim 12, wherein the second bone is in the mid-foot region of the foot.

* * * * *